(12) United States Patent
Bristow

(10) Patent No.: US 12,365,671 B2
(45) Date of Patent: Jul. 22, 2025

(54) CRYSTALLINE HYDRATE OF TOPRAMEZONE SODIUM SALT AND PREPARATION METHOD THEREFOR

(71) Applicant: ROTAM AGROCHEM INTERNATIONAL COMPANY LIMITED, Chai Wan (HK)

(72) Inventor: James Timothy Bristow, Chai Wan (HK)

(73) Assignee: ALBAUGH, LLC, Ankeny, IA (US)

( * ) Notice: Subject to any disclaimer, the term of this patent is extended or adjusted under 35 U.S.C. 154(b) by 1198 days.

(21) Appl. No.: 17/175,112

(22) Filed: Feb. 12, 2021

(65) Prior Publication Data

US 2022/0259192 A1    Aug. 18, 2022

(51) Int. Cl.
| | | |
|---|---|---|
| C07D 413/10 | (2006.01) | |
| A01N 25/04 | (2006.01) | |
| A01N 25/14 | (2006.01) | |
| A01N 25/30 | (2006.01) | |
| A01N 43/80 | (2006.01) | |

(52) U.S. Cl.
CPC ........... *C07D 413/10* (2013.01); *A01N 25/04* (2013.01); *A01N 25/14* (2013.01); *A01N 25/30* (2013.01); *A01N 43/80* (2013.01); *C07B 2200/13* (2013.01)

(58) Field of Classification Search
CPC ...... C07D 413/10; A01N 25/04; A01N 25/14; A01N 25/30; A01N 43/80; C07B 2200/13; A01P 13/00
See application file for complete search history.

(56) References Cited

U.S. PATENT DOCUMENTS

| 8,017,556 B2 * | 9/2011 | Gebhardt ............. C07D 413/10 548/240 |
| 2002/0025910 A1 | 2/2002 | von Deyn |
| 2010/0075853 A1 | 3/2010 | Krapp |

FOREIGN PATENT DOCUMENTS

CN    1117750 C    8/2003

OTHER PUBLICATIONS

Moore, M. Dissertation. Evaluation of topramezone for use in rice (*Oryza sativa* L.) production. University of Arkansas, 2019. (Year: 2019).*
Bhupechandra et al. Plant, Cell & Environment. Mar. 4, 2024. (Year: 2024).*
Junguo Li, Chaohui Pan, "Topramezone Synthesis Research Progress" [J]. Pesticides, 2020, 59(8): 547-555.

* cited by examiner

*Primary Examiner* — Scarlett Y Goon
*Assistant Examiner* — Sophia Marie Taylor
(74) *Attorney, Agent, or Firm* — Dickinson Wright PLLC

(57) ABSTRACT

A crystalline hydrate of topramezone sodium salt is provided. A preparation method for the crystalline hydrate of topramezone sodium salt and herbicidal compositions including the crystalline hydrate of topramezone sodium salt are also provided.

14 Claims, 3 Drawing Sheets

CRYSTALLINE HYDRATE OF TOPRAMEZONE SODIUM SALT AND PREPARATION METHOD THEREFOR

TECHNICAL FIELD OF THE INVENTION

The invention relates to the field of agro-chemistry, in particular to a crystalline hydrate of topramezone sodium salt and a preparation method thereof.

BACKGROUND OF THE INVENTION

Topramezone is a highly selective phenyl-pyrazolyl-ketone herbicide developed by BASF Corporation of Germany. It belongs to the class of 4-Hydroxyphenylpyruvate dioxygenase (HPPD) inhibitors. It can effectively prevent gramineous weeds and broadleaf weeds in maize field around the world.

The chemical structure of topramezone is:

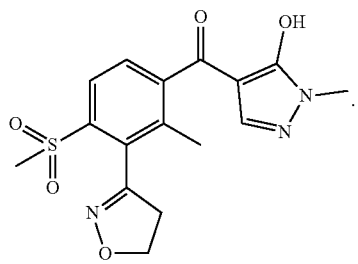 [SMILES: Cc1c(C(=O)c2cnn(C)c2O)ccc(S(C)(=O)=O)c1C1=NOCC1]

Synthesis of topramezone has been reported and the compound is difficult to synthesize. Junguo Li, Chaohui Pan and their team has described in "Topramezone Synthesis Research Progress [J]. Pesticides, 2020, 59(8): 547-555" the synthesis processes and they have analyzed the costs and safety of different production techniques.

With regard to the synthesis of topramezone, two main methods have been reported and they are (1) carbonylation and (2) rearrangement of an esterified carboxyl acyl chloride.

The synthesis reaction by carbonylation (1) is described in Reaction Route 1.

Reaction Route 1.

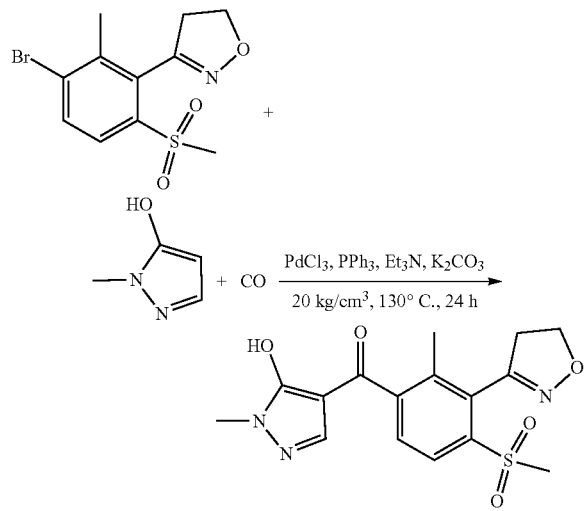

The synthesis reaction by rearrangement of an esterified carboxyl acyl chloride (2) is described in Reaction Route 2.

Reaction Route 2.

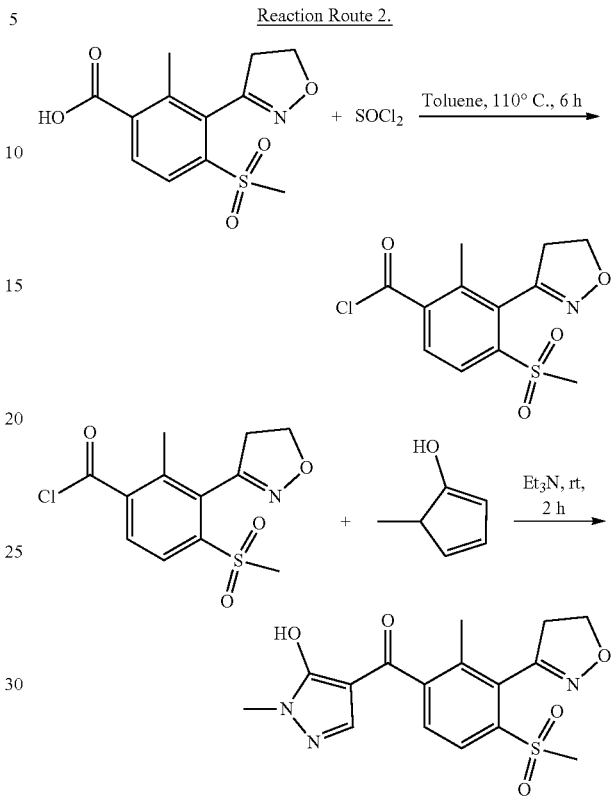

CN1011177750C reports the structure of topramezone, inorganic salt thereof and the preparation method for a compound like topramezone potassium salt. It also reports that the type of salt of topramezone is not important; whether it is cationic salt or salt addition, it does not adversely affect the herbicidal activity of the compound. Meanwhile, in the preparation embodiment of the patent, anhydrous dioxane was used as the solvent, triethylamine was used as the acid-binding agent, methylsulfonyl chloride and 5-hydroxy-pyrazole were bonded, potassium carbonate was added to the system, the system was refluxed to obtain a compound like topramezone potassium salt, and if no acid adjustment is carried out, anhydrous topramezone will be obtained after solvent removal.

The preparation of aqueous topramezone sodium salt is reported in US2010075853A, the efficacy is also reported. The activity of the topramezone sodium salt aqueous solution was equal to or even higher than topramezone acid. However, there are some disadvantages in the form of the aqueous topramezone sodium salt. For example, the content of the topramezone is limited to the solubility of itself and the solution thus cannot possess a high topramezone content; furthermore, aqueous formulations require high packaging, storage, and transportation costs.

Therefore, the industry needs a more suitable form of topramezone in order to achieve higher efficacy while having sufficient solubility and reduced packaging, storage, and transportation costs.

DETAILED DESCRIPTION

The inventor has unexpectedly found that the crystalline hydrate (2.5 hydrate) of topramezone sodium salt has significantly better stability, and the crystalline hydrate has obvious advantages in terms of formulation preparation; it can effectively resolve the dusty situation during jet pulverization, reduce granulation difficulties, etc.

Based on the above discovery, in a first aspect, the present invention provides a crystalline 2.5 hydrate of topramezone sodium salt as shown in formula I.

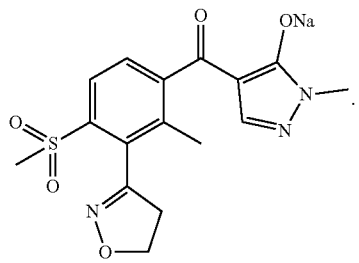

The crystalline hydrate is subjected to single crystal diffraction analysis which shows an orthogonal crystal with the following parameters:

| Parameters | Values |
| --- | --- |
| Space group | Pbcn |
| a | 2563.60(15) pm |
| b | 953.24(7) pm |
| c | 1566.96(10) pm |
| α | 90° |
| β | 90° |
| γ | 90° |
| Volume | 3829.2(4) am$^3$ |
| Z | 4 |

The parameters shown in the table have the following meanings:
a, b, c=edge length of unit cell
α, β, γ=corresponding angle
Z=number of molecules in a unit cell Further analysis of the single crystal characterization data shows that the crystalline hydrate of topramezone sodium salt is a crystalline 2.5 hydrate as shown in the ellipsoid of FIG. 1. From the structure, the sodium atom and hydroxyl group on the pyrazole ring and the adjacent carbonyl groups together form the topramezone sodium salt which possesses 2 water molecules, and share another one water molecule with the adjacent topramezone sodium salt molecule, so that a crystalline hydrate with 2.5 water molecules is integrally formed, and the structural formula of the crystalline hydrate is shown as follows:

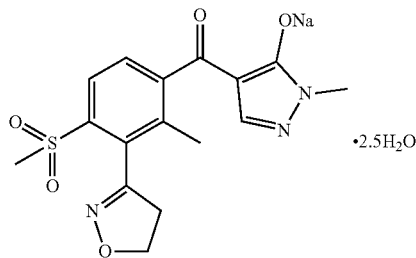

The crystalline 2.5 hydrate of topramezone sodium salt of the present invention has huge advantages over the anhydrous form of topramezone sodium salt with respect to formulation preparation. The anhydrous topramezone sodium salt can be prepared according to the preparation method of the topramezone potassium salt alike compound reported in US2002025910A. Experiments show that the anhydrous topramezone sodium salt was easy to agglomerate during jet pulverization, and the environment became severely dusty. Furthermore, the formulation preparation process is difficult. For example, when preparing the soluble granule, creaming and caking of the ingredients frequently occurs, and granulation thus becomes difficult. However, the crystalline 2.5 hydrate of topramezone sodium salt can be granulated easily. Through thermal storage (accelerated stability) experiments on the formulation products, it has been surprisingly found that the formulation prepared using the crystalline 2.5 hydrate of topramezone sodium salt is more stable than the anhydrous form.

A second aspect of the present invention provides a method for preparing the crystalline 2.5 hydrate of topramezone sodium salt. The preparation method of the crystalline hydrate can be carried out by the method comprises the following steps:
1) Forming topramezone sodium salt aqueous solution by mixing from 1:0.1 to 1:10 stoichiometric ratio of topramezone and sodium hydroxide; and
2) Crystallizing the crystalline hydrate by maintaining the temperature of the resulting solution of step 1) at from −15° C. to 15° C., preferably from −10° C. to 10° C.

Preferably, the preparation method comprises the following steps:
1) Topramezone and water are added to a reaction apparatus and sodium hydroxide is added to the solution at a stoichiometric ratio of from 1:0.9 to 1:1.2 of topramezone to sodium hydroxide, the solution mixture is stirred at from 20° C. to 60° C. to form the topramezone sodium salt aqueous solution; and
2) The resulting solution of step 1) is cooled to ambient temperature and subsequently cooled to −15° C. to 15° C. in an ice-salt bath, the solution is stirred until crystallization is stopped, and the resulting slurry is filtered and dried to obtain the crystalline hydrate.

In the abovementioned step 1), topramezone can be obtained by the process described in US2002025910A; and the weight ratio of topramezone to water is from 1:3 to 1:8, preferable from 1:4 to 1:5.

In the abovementioned step 2), the temperature of the solution is maintained at from −15° C. to 15° C. in an ice-salt bath, preferably from −10° C. to 10° C.

In a preferred aspect, 50% to 80% of the water of the topramezone sodium salt aqueous solution of step 1) is removed by rotary evaporation, one or more polar solvents is added to the solution and mixed to perform mixed solvent crystallization. The steps are specified as follows:
1) Topramezone and water are added to a reaction apparatus and sodium hydroxide is added to the solution at a stoichiometric ratio of from 1:0.9 to 1:1.2 of topramezone to sodium hydroxide, the solution mixture is stirred at from 20° C. to 60° C. to form the topramezone sodium salt aqueous solution;
2) 50% to 80% of the water of the topramezone sodium salt aqueous solution of step 1) is removed by rotary evaporation, one or more polar solvent is added to the solution and optionally heated to form a clear solution; and
3) The resulting solution of step 2) is cooled to ambient temperature and subsequently cooled to −15° C. to 15° C. in an ice-salt bath, the solution is stirred until crystallization is stopped, and the resulting slurry is filtered and dried to obtain the crystalline hydrate;

wherein the weight ratio of topramezone to water at step 1) is from 1:4 to 1:8, preferable from 1:4 to 1:6; the one or more polar solvent of step 2) is selected from small molecular alcohol solvents, preferably selected from methanol, ethanol, isopropanol, n-butanol, tert-butanol, and/or mixtures thereof; and the preferred ice-salt bath temperature of step 3) is from −10° C. to 10° C.

The crystalline 2.5 hydrate of the present invention is characterized by single crystal diffraction, powder XRD and Karl Fischer titration. The XRD pattern of the crystalline 2.5 hydrate of topramezone sodium salt of the present invention is obtained by fitting the single crystal characterization data. The XRD pattern exhibits at least 3, 5, 8, or preferably all of the following 10 reflexes, at 2θ±0.2° degree in an X-ray powder diffractogram: 11.14±0.2°, 13.72±0.2°, 14.91±0.2°, 15.16±0.2°, 18.51±0.2°, 19.36±0.2°, 19.76±0.2°, 20.56±0.2°, 21.78±0.2°, and 22.40±0.2°. Preferable, the crystalline 2.5 hydrate of topramezone sodium salt of the present invention exhibits the following reflexes, at 2θ±0.2° degree: 11.136±0.2°, 13.718±0.2°, 19.360±0.2°, 20.555±0.2°, 21.782±0.2°, and 22.399±0.2°. More preferable, the crystalline 2.5 hydrate of topramezone sodium salt of the present invention exhibits the following reflexes, at 2θ±0.2° degree: 11.136±0.2°, 13.718±0.2°, 19.360±0.2°, 20.555±0.2°, 21.782±0.2°, 22.399±0.2°, and 28.362±0.2°.

The fitted XRD pattern of the crystalline 2.5 hydrate of topramezone sodium salt of the present invention is shown in FIG. 2.

A third aspect of the present invention provides a herbicidal composition comprising a crystalline 2.5 hydrate of topramezone sodium salt, one or more filler, and/or one or more surfactant.

It is known in the art that the content of an active ingredient in an aqueous formulation is limited to the solubility of the active ingredient; it is further limited by the packaging, storage and transportation costs. The crystalline 2.5 hydrate of topramezone sodium salt of the present the invention overcomes such limitations. In addition, the crystalline hydrate of the invention can be subjected to formulation preparation without any problems, compared to the anhydrous topramezone sodium salt form. Furthermore, formulations prepared from the crystalline 2.5 hydrate of topramezone sodium salt possess better heat storage stability.

The herbicidal compositions according to the present invention comprise the crystalline 2.5 hydrate of topramezone sodium salt in the following percentage by weight: from 1% to 90%, preferably from 10% to 90%, preferably from 20% to 90%, more preferably from 30% to 90%, more preferably from 50% to 90%, and still more preferably from 50% to 80%.

The herbicidal compositions according to the present invention can be any suitable formulation, including a soluble granule (SG), a water dispersible granule (WG), a wettable powder (WP), an oil dispersion (OD) or a dispersible tablet.

The "filler" of the present invention can be in the form of a solid carrier or a liquid carrier.

Suitable liquid carriers include, but are not limited to, water, N,N-dimethylformamide, dimethyl sulfoxide, N-alkylpyrrolidone, ethylene glycol, polypropylene glycol, propylene carbonate, dibasic esters, paraffines, alkylbenzenes, alkyl naphthalenes, glycerol, triacetine, oils of olive, castor, linseed, sesame, corn, peanut, cotton-seed, soybean, rapeseed and coconut, ketones such as cyclohexanone, 2-heptanone, isophorone and 4-hydroxy-4-methyl-2-pentanone, acetates such as hexyl acetate, heptyl acetate and octyl acetate, water and alcohols such methanol, cyclohexanol, decanol, benzyl alcohol and tetrahydrofurfuryl alcohol and mixtures thereof.

Suitable solid carriers can be water-soluble or water-insoluble. Water-soluble solid carriers include, but are not limited to, salts such as alkali metal phosphates (e.g., sodium dihydrogen phosphate), alkaline earth metal phosphates, sulfates of sodium, potassium, magnesium and zinc, sodium and potassium chloride, sodium acetate, sodium carbonate and sodium benzoate, and sugars and sugar derivatives such as sorbitol, lactose, sucrose and mannitol. Examples of water-insoluble solid carriers include, but are not limited to clays, synthetic and diatomaceous silicas, calcium and magnesium silicates, titanium dioxide, alumina, calcium oxide and zinc oxide and mixtures thereof.

The surfactants can be wetting agents, dispersants or thickeners.

Suitable wetting agents include, but are not limited to, alkyl sulfosuccinates, laureates, alkyl sulfates, phosphate esters, acetylenic diols, ethoxyfluornated alcohols, ethoxylated silicones, alkyl phenol ethyoxylates, benzene sulfonates, alkyl-substituted benzene sulfonates, alkyl alpha-olefin sulfonates, naphthalene sulfonates, alkyl-substituted napthalene sulfonates, condensates of naphthalene sulfonates and alkyl-substituted naphthalene sulfonates with formaldehyde, alcohol ethoxylates, and mixtures thereof. Alkylnapthalene sulfonates is particularly useful for the compositions of the invention.

Dispersants include, but are not limited to, sodium, calcium and ammonium salts of ligninsulfonates (optionally polyethoxylated); sodium and ammonium salts of maleic anhydride copolymers; sodium salts of condensed phenolsulfonic acid; and naphthalene sulfonate-formaldehyde condensates. Of note are compositions comprising up to 10% by weight of dispersant. Ligninsulfonates such as sodium ligninsulfonate are particularly useful for the composition of the invention.

Thickeners include, but are not limited to guar gum, pectin, casein, carrageenan, xanthan gum, alginates, methylcellulose, hydroxyethyl-cellulose, hydroxypropylcellulose, carboxymethylcellulose, and mixtures thereof. Synthetic thickeners include derivatives of the former categories, and also polyvinyl alcohols, polyacrylamides, polyvinylpyrrolidones, various polyethers, their copolymers as well as polyacrylic acids and their salts, and mixtures thereof.

Other formulation ingredients can also be used in the present invention, such as dyes, drying agents, preservatives, antioxidants, carriers, and the like. These ingredients are known to those skilled in the art.

A fourth aspect of the present invention provides the use of the herbicidal compositions in controlling undesirable plant growth. The resulting compositions are particularly suitable for preventing unwanted plant growth on non-crop areas. The herbicidal compositions can prevent and treat gramineous and broadleaf weeds in cereal crops such as wheat, rye, barley, millet, oat or black wheat, and corn, without causing any significant damage to the crop plant. The effect is particularly observed at low application rates.

In particular, the herbicidal compositions are used for preventing and treating the following weeds: *Digitaria*, barnyard grass, *Eleusine indica, Clinacanthus nutans, Setaria viridis, Chenopodium serotinum, Polygonum, Abutilon theophrasti, Portulaca oleracea, Xanthium strumarium, Solanum nigrum*, and the like. According to example embodiments, the herbicidal compositions are used to control the following undesirable plants: fern, barnyard grass, steak grass, wild Paris, dog-tail herb, *chenopodium quinoa, polygonum capitatum, cimicifugae*, purslane, cocklebur, and/or black nightshade in a maize field.

A fifth aspect of the present invention provides a method for controlling undesirable plant growth, comprising applying the herbicidal compositions of the present invention to undesirable plants or the locus thereof.

Application methods can be pre-emergence application, post-emergence application, or apply together with crop seeds, in a herbicidally effective amount to undesirable plants or the locus thereof. If certain crop plants are poor in tolerance to the active compound, spray equipment can be used for directional spraying so that the active compound does not contact the leaves of sensitive crop plants as much as possible, while the active compound reaches the leaves of undesired plants growing below the crop plants or the surface of soil.

In order to broaden the efficacy spectrum and achieve a synergistic effect, the herbicidal compositions can be mixed with many representative weeding or growth-regulating active compound groups prior to application, for example by tank-mixing method.

EXAMPLES

Examples of the present invention are described below. It should be understood by those skilled in the art that the described examples are merely to aid in understanding the present invention and should not be taken as limitations.

Example 1: Preparation of Anhydrous Topramezone Sodium Salt

In a protective atmosphere at room temperature, 41.3 g (0.13 mol) 2-methyl-3-(4,5-dihydroisoxazol-3-yl)-4-methylsulfonylbenzoic acid chloride in 375 ml anhydrous dioxane and 13.56 g (0.134 mol) triethylamine in 375 ml anhydrous dioxane were added dropwise simultaneously to 300 ml of anhydrous dioxane which contained 12.74 g (0.13 mol) 5-hydroxy-1-methylpyrazole. The reaction mixture was stirred at room temperature for 2 hours, filtered by silica gel, and washed with dioxane. The eluent was concentrated in vacuum to about 500 ml, and 49.0 g (0.13 mol) of dried finely powdered sodium carbonate was added to the concentrate. After heating at reflux for 7 hours, the solvent was removed under reduced pressure.

The residue was added into about 700 ml of anhydrous methanol, insoluble components were filtered out, the mother liquor was subjected to rotary evaporation to remove the solvent, and 49.0 g (93% yield) of anhydrous topramezone sodium salt (KF: water content <1%) was obtained.

Example 2: Preparation of Crystalline 2.5 Hydrate of Topramezone Sodium Salt 22.0 g of topramezone (0.06 mol) was added into a reaction bottle containing 100 ml of water, 4.9 g (0.06 mol) of sodium hydroxide 50% solution was added dropwise at room temperature to the reaction bottle, and the solution was heated to 50° C. and stirred until the solution became clear. The temperature of the solution was slowly reduced to room temperature, then using an ice bath to cool to 0° C., the temperature was maintained between −5° C. and 5° C., and the solution was rested aside in the ice bath until crystallization was completed and solids were separated. The resulting product was filtered and dried in a vacuum oven at 50° C. 22.8 g crystalline hydrate of topramezone sodium salt was obtained and the yield was 90% (KF:water content 10.8%).

Figure 1:
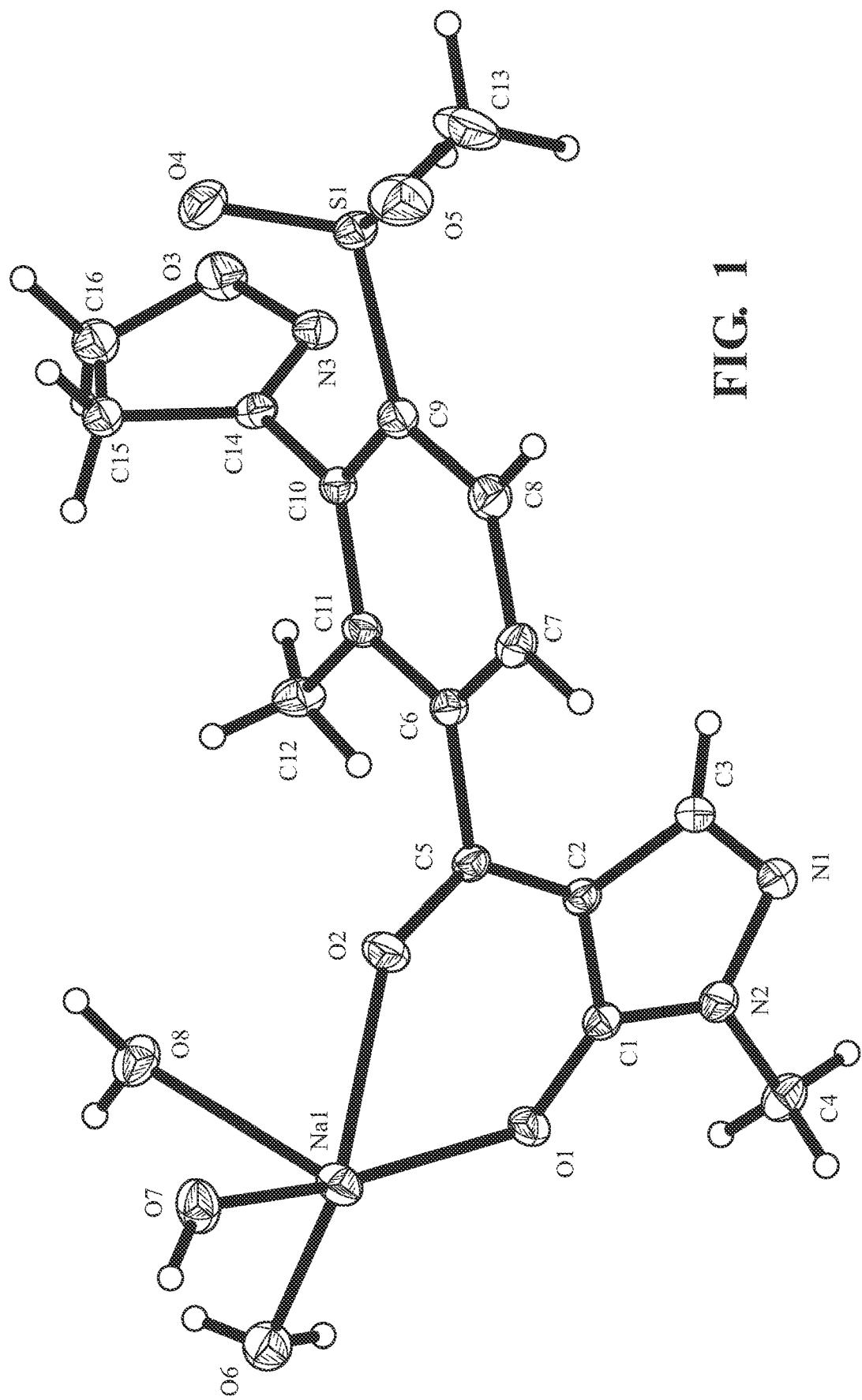
FIG. 1 is an ellipsoidal diagram of the crystalline 2.5 hydrate of topramezone sodium salt provided by the present invention.
Figure 2:
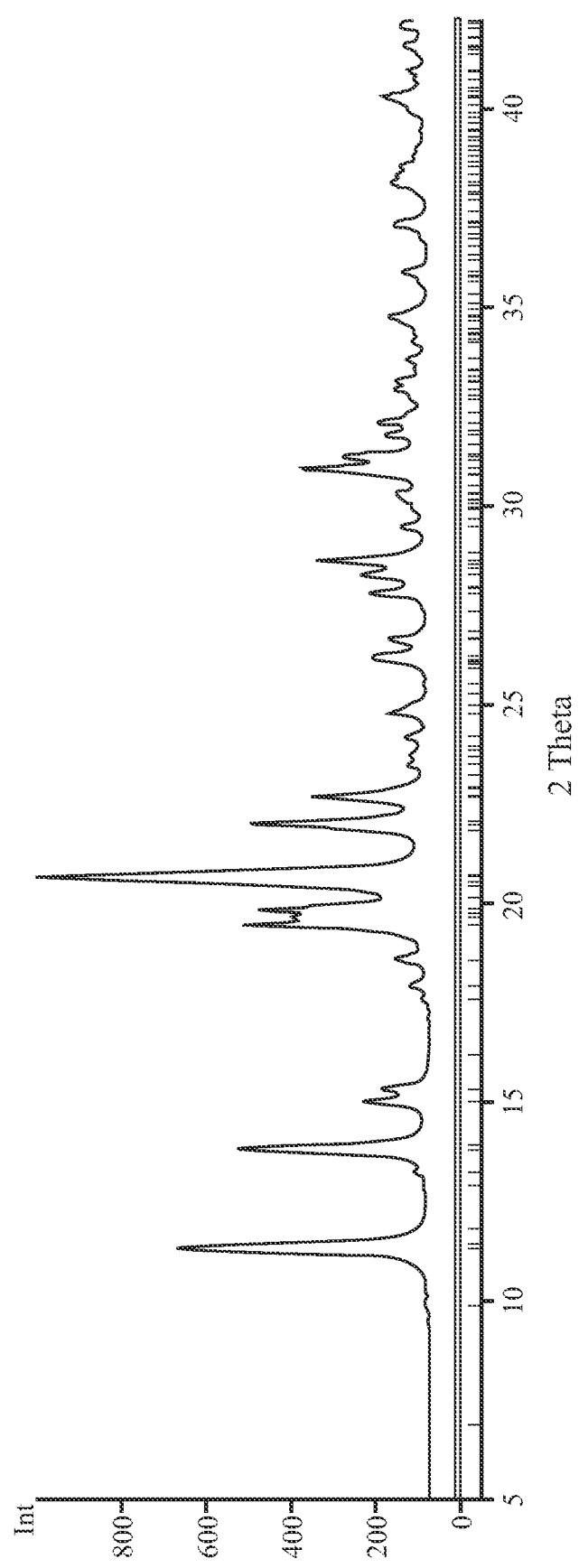
FIG. 2 is a fitted XRD pattern of the crystalline 2.5 hydrate of topramezone sodium salt provided by the present invention.
Figure 3:
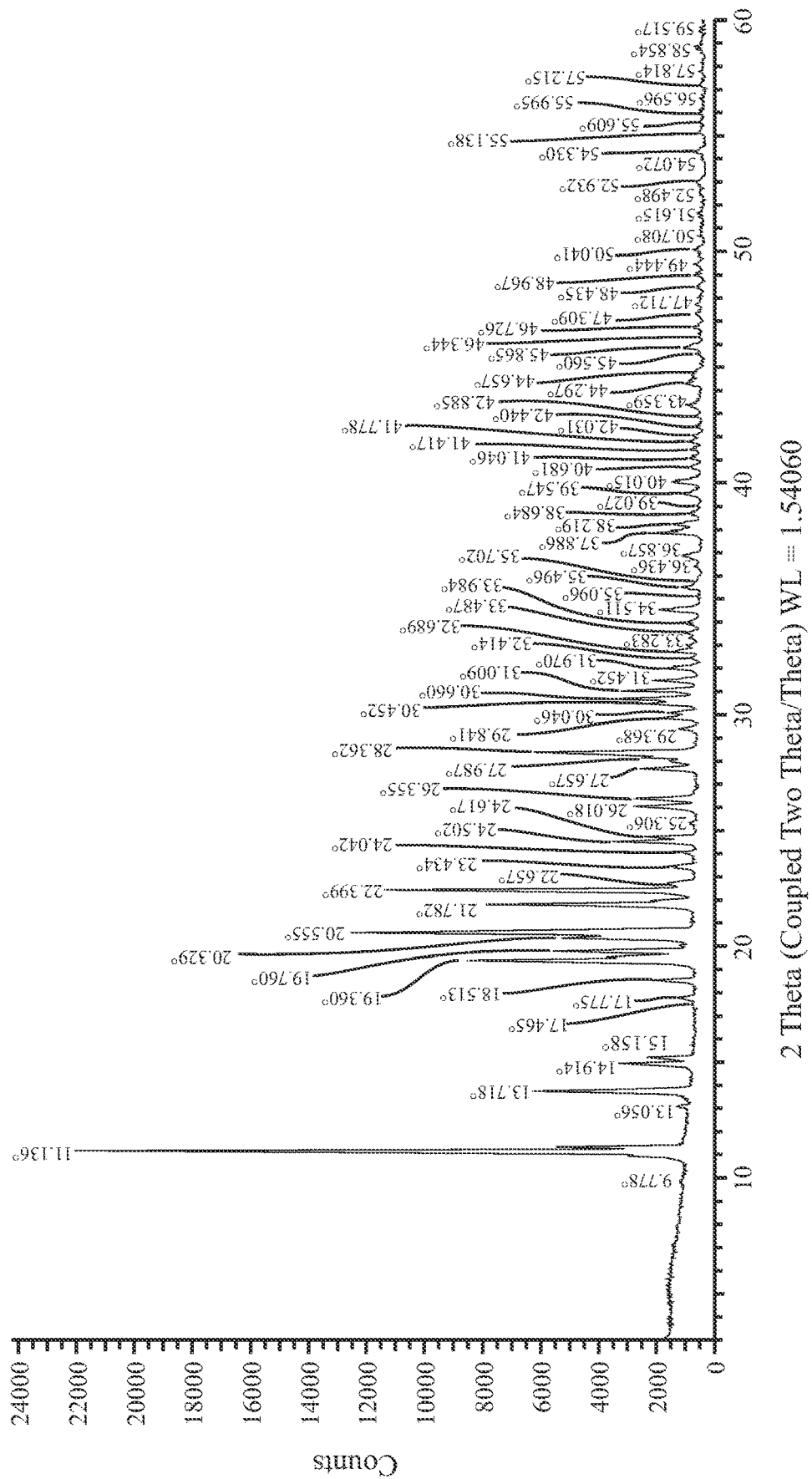
FIG. 3 is a measured XRD pattern of the crystalline 2.5 hydrate of topramezone sodium salt provided by the invention.

The solid particles obtained by the example were analyzed by X-ray powder diffraction (XRD), the graph is shown in FIG. 3, and it was found to be the crystalline 2.5 hydrate of topramezone sodium salt as shown in FIG. 2.

Example 3: Preparation of Crystalline 2.5 Hydrate of Topramezone Sodium Salt 22.0 g of topramezone (0.06 mol) was added into a reaction bottle containing 90 ml of water, 4.9 g (0.06 mol) of sodium hydroxide 50% solution was added dropwise at room temperature to the reaction bottle, and the solution was heated to 50° C. and stirred until the solution became clear, and pressure was reduced to remove 30 g of water. 50 g of methanol was added to the solution and the solution was heated until it became clear. The temperature of the solution was slowly reduced to room temperature, then using an ice bath to cool to −5° C., the temperature was maintained between −5° C. and 0° C., and the solution was rested aside in the ice bath until crystallization was completed and solids were separated. The resulting product was filtered and dried in a vacuum oven at 60° C. 22.8 g crystalline hydrate of topramezone sodium salt as shown in formula I was obtained and the yield was 93% (KF:water content 10.9%).

The solid particles obtained by the example were analyzed by X-ray powder diffraction (XRD), and it had substantially the same pattern as the graph shown in FIG. 3, which indicates it was the crystalline 2.5 hydrate of topramezone sodium salt.

Example 4: Preparation of Crystalline 2.5 Hydrate of Topramezone Sodium Salt 20.0 g of anhydrous topramezone sodium salt obtained from Example 1 was added into a reaction bottle containing 80 ml of water, the solution was stirred and heated to between 60° C. and 70° C. 5 ml to 10 ml of water may be added to the solution to dissolve any insoluble materials, if any. The temperature of the solution was slowly reduced to room temperature, then using an ice bath to cool to 0° C., the temperature was maintained between −5° C. and 0° C., and the solution was rested aside in the ice bath until crystallization was completed and solids were separated. The resulting product was filtered and dried in a vacuum oven at 50° C. 20.1 g crystalline hydrate of topramezone sodium salt was obtained and the yield was 920 (KF:water content 10.8%).

The solid particles obtained by the example were analyzed by X-ray powder diffraction (XRD) and it had substantially the same pattern as the graph shown in FIG. 3, which indicates it was the crystalline 2.5 hydrate of topramezone sodium salt.

Example 5: Preparation of d350 Water Dispersible Granule (WDG) Formulation

All components listed in Table 1 below were uniformly mixed, crushed into powder with an average particle size of about 3 m using a jet pulverizer. A sufficient amount of water was added in order to obtain an extrudable paste. The resulting paste was passed through and extruded from a mold or screen to form an extrudate. The wet extrudate was dried under 45° C. in a vacuum oven and screened by a 0.7 mm–2 mm screen to obtain product granules.

TABLE 1

| Ingredients | Weight % Sample 1 | Sample 2 | Function |
| --- | --- | --- | --- |
| Crystalline 2.5 hydrate of topramezone sodium salt (97%) | 36.08 | 0 | Active compound |
| Anhydrous topramezone sodium salt (95%) | 0 | 36.84 | Active compound |
| Polyoxyethylene triphenyl phosphoric acid calcium | 6 | 6 | Dispersing agent |
| Sodium Alkylnaphthalenesulfonate | 2 | 2 | Dispersing agent |
| Carboxymethyl cellulose | 3 | 3 | Thickener |
| Polyethylene glycol | 3 | 3 | Disintegrant |
| White carbon black | Balanced to 100% | Balanced to 100% | Adjuvant carrier |

Example 6: Preparation of 5000 Wettable Powder (WP) Formulation

All components listed in Table 2 below were uniformly mixed, crushed into powder with an average particle size of about 3 μm using a jet pulverizer to obtain a wettable powder formulation.

TABLE 2

| Ingredients | Weight % Sample 3 | Sample 4 | Function |
| --- | --- | --- | --- |
| Crystalline 2.5 hydrate of topramezone sodium salt (97%) | 51.55 | 0 | Active compound |
| Anhydrous topramezone sodium salt (95%) | 0 | 52.63 | Active compound |
| Polyoxyethylene triphenyl phosphoric acid calcium | 6 | 6 | Dispersing agent |
| Alkylphenol Ethoxylates | 3 | 3 | Dispersing agent |
| Sodium Alkylnaphthalenesulfonate | 2 | 2 | Wetting agent |
| White carbon black | 5 | 5 | Adjuvant carrier |
| Diatomite | Balanced to 100% | Balanced to 100% | Adjuvant carrier |

Example 7: Preparation of 48% Soluble Granule (SG) Formulation

All components listed in Table 3 below were uniformly mixed, crushed into ultra-fine powder with an average particle size of about less than 44 microns using a ultra-fine pulverizer.

TABLE 3

| Ingredients | Weight % Sample 5 | Sample 6 | Function |
| --- | --- | --- | --- |
| Crystalline 2.5 hydrate of topramezone sodium salt (97%) | 49.48 | 0 | Active compound |
| Anhydrous topramezone sodium salt (95%) | 0 | 50.52 | Active compound |
| Sodium Alkylnaphthalenesulfonate | 2 | 2 | Wetting agent |
| Alkylnaphthalene sulfonic acid condensation polymer | 12 | 12 | Dispersing agent |
| Sodium triphosphate | 2 | 2 | Thickener |
| Sucrose | Balanced to 100% | Balanced to 100% | Excipient |

Example 8: Preparation of 5200 Oil Dispersion (OD) Formulation

All components listed in Table 4 below were uniformly mixed by a high shear mixer, then grinded or milled to obtain a topramezone sodium salt oil dispersion.

TABLE 4

| Ingredients | Weight % Sample 7 | Sample 8 | Function |
| --- | --- | --- | --- |
| Crystalline 2.5 hydrate of topramezone sodium salt (97%) | 53.61 | 0 | Active compound |
| Anhydrous topramezone sodium salt (95%) | 0 | 54.74 | Active compound |
| Geronol VO/01 | 300 | 300 | Emulsifier |
| HDK N20 | 30 | 30 | Thickener |
| BREAK-THRU AF9902 | 15 | 15 | Anti-foaming agent |
| MORWET D-450 POWDER | 40 | 40 | Wetting dispersant |
| Corn Oil | Balanced to 100% | Balanced to 100% | Solvent |

Example 9: Formulations Performance Comparison

Samples 1, 2, 3, 4, 5, 6, 7 and 8 prepared in Examples 5 to 8 were stored separately at 54° C. for 2 weeks. Differences in sample characteristics before storage and after storage were recorded and compared, and the results of the comparison are shown in Table 5.

TABLE 5

| Samples | Active Compounds and Formulations | Change in Characteristics |
| --- | --- | --- |
| Sample 1 | 35% Crystalline 2.5 hydrate of topramezone sodium salt WDG | None |
| Sample 2 | 35% Anhydrous topramezone sodium salt WDG | Partially caked |
| Sample 3 | 50% Crystalline 2.5 hydrate of topramezone sodium salt WP | None |
| Sample 4 | 50% Anhydrous topramezone sodium salt WP | Caked |
| Sample 5 | 48% Crystalline 2.5 hydrate of topramezone sodium salt SG | None |
| Sample 6 | 48% Anhydrous topramezone sodium salt SG | Partially creamed |
| Sample 7 | 52% Crystalline 2.5 hydrate of topramezone sodium salt OD | None |
| Sample 8 | 52% Anhydrous topramezone sodium salt OD | Caked and precipitated |

It can be seen from the table that the formulations prepared by the crystalline 2.5 hydrate of topramezone sodium salt has better stability properties after heat accelerated storage, and the formulations prepared from the anhydrous topramezone sodium salt has caking or creaming phenomenon after the storage conditions.

It should be appreciated that the foregoing description of the embodiments has been provided for purposes of illustration. In other words, the subject disclosure it is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varies in many ways. Such variations are not to be regarded as a departure from the disclosure, and all such modifications are intended to be included within the scope of disclosure.

The invention claimed is:

1. A crystalline 2.5 hydrate of topramezone sodium salt of formula I:

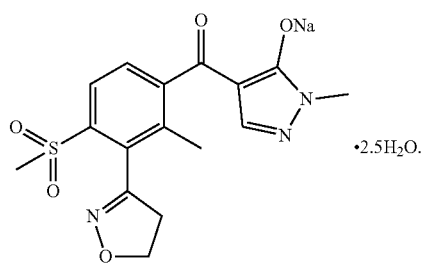

I

2. The crystalline hydrate of claim 1 wherein said crystalline hydrate is orthorhombic and has the following parameters:

| Parameters | Values |
| --- | --- |
| Space group | Pbcn |
| a | 2563.60(15) pm |
| b | 953.24(7) pm |
| c | 1566.96(10) pm |
| α | 90° |
| β | 90° |
| γ | 90°. |

3. An herbicidal composition comprising the crystalline hydrate of claim 1 and fillers and/or surfactants.

4. The herbicidal composition of claim 3 wherein the composition is in the form of a soluble granule (SG), a water dispersible granule (WG), a wettable powder (WP), an oil dispersion (OD) or a dispersible tablet.

5. A method for preparing the crystalline hydrate of claim 1 comprising the following steps:
   1) forming topramezone sodium salt aqueous solution by mixing from 1:0.9 to 1:1.2 stoichiometric ratio of topramezone and sodium hydroxide; and
   2) crystallizing the crystalline hydrate by maintaining the temperature of the resulting solution of step 1) at from −15° C. to 15° C.

6. The method of claim 5 wherein:
   at step 1): topramezone and water are added to a reaction apparatus and sodium hydroxide is added to the solution at a stoichiometric ratio of from 1:0.9 to 1:1.2 of topramezone to sodium hydroxide, the solution mixture is stirred at from 20° C. to 60° C. to form the topramezone sodium salt aqueous solution; and
   at step 2): the resulting solution of step 1) is cooled to ambient temperature and subsequently cooled to −15° C. to 15° C. in ice-salt bath, the solution is stirred until crystallization is stopped, and the resulting slurry is filtered and dried to obtain the crystalline hydrate.

7. The method of claim 5, wherein:
   at step 1): the stoichiometric ratio of topramezone to sodium hydroxide is from 1:1 to 1:1.1.

8. The method of claim 5 wherein:
   at step 1): the weight ratio of topramezone to water is from 1:3 to 1:8.

9. The method of claim 5 wherein:
   at the end of step 1) 50% to 80% of the water of the topramezone sodium salt aqueous solution is removed by rotary evaporation, one or more polar solvent is added to the solution and optionally heated to form a clear solution.

10. The method of claim 9 wherein:
    at step 1): the weight ratio of topramezone to water is from 1:4 to 1:8.

11. The method of claim 9 wherein the one or more polar solvent is selected from methanol, ethanol, isopropanol, n-butanol, tert-butanol, and/or mixtures thereof.

12. A method for the control of plant growth, the method comprising applying an herbicidal composition including the crystalline hydrate of claim 1 to at least one plant or the locus thereof.

13. The method of claim 12, wherein the at least one plant is a gramineous weed or broadleaf weed in a maize field.

14. The method of claim 12, wherein the at least one plant is fern, barnyard grass, steak grass, wild Paris, dog-tail herb, *chenopodium quinoa, polygonum capitatum, cimicifugae,* purslane, cocklebur, or black nightshade in a maize field.

* * * * *